(12) United States Patent
Robinson et al.

(10) Patent No.: US 8,192,418 B2
(45) Date of Patent: Jun. 5, 2012

(54) RELEASING A MATERIAL WITHIN A MEDICAL DEVICE VIA AN OPTICAL FEEDTHROUGH

(75) Inventors: Reginald D. Robinson, Plymouth, MN (US); David D. Differding, Edina, MN (US); James A. Johnson, Blaine, MN (US); Bernard Q. Li, Plymouth, MN (US); Gerald G. Lindner, Lino Lakes, MN (US); Brad C. Tischendorf, Minneapolis, MN (US); Andrew J. Thom, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 495 days.

(21) Appl. No.: 12/401,267

(22) Filed: Mar. 10, 2009

(65) Prior Publication Data

US 2010/0234825 A1 Sep. 16, 2010

(51) Int. Cl.
*A61M 5/32* (2006.01)

(52) U.S. Cl. ........ 604/415; 604/403; 600/372; 600/373; 600/374; 600/310; 600/377; 600/381; 600/393; 600/394; 600/325; 600/327; 600/333; 607/115; 607/119; 607/122; 607/36; 102/201

(58) Field of Classification Search .................. 604/403, 604/415; 600/372–374
See application file for complete search history.

(56) References Cited

U.S. PATENT DOCUMENTS

| | | | |
|---|---|---|---|
| 4,340,097 A | | 7/1982 | Ammann et al. |
| 5,902,326 A | | 5/1999 | Lessar et al. |
| 6,047,643 A | * | 4/2000 | Benner et al. ................. 102/201 |
| 6,068,617 A | | 5/2000 | Richmond |
| 6,293,922 B1 | | 9/2001 | Haase |
| 6,626,867 B1 | * | 9/2003 | Christenson et al. ......... 604/153 |
| 6,635,049 B1 | * | 10/2003 | Robinson et al. ........... 604/891.1 |
| 6,743,204 B2 | * | 6/2004 | Christenson et al. ......... 604/151 |
| 2002/0035385 A1 | | 3/2002 | Deziz |
| 2005/0080465 A1 | | 4/2005 | Zelickson et al. |
| 2006/0259090 A1 | | 11/2006 | He et al. |
| 2007/0134974 A1 | | 6/2007 | Starke et al. |

FOREIGN PATENT DOCUMENTS

| | | |
|---|---|---|
| DE | 3330421 A1 | 3/1985 |
| EP | 1 234 595 A2 | 8/2002 |
| EP | 1621177 A1 | 2/2006 |
| WO | WO2006/034814 A1 | 6/2006 |
| WO | 2008121298 A1 | 10/2008 |

OTHER PUBLICATIONS

U.S. Patent Application "Posture State Management for Posture-Responsive Therapy" having U.S. Appl. No. 61/080,089, filed Jul. 11, 2008.

(Continued)

*Primary Examiner* — Tatyana Zalukaeva
*Assistant Examiner* — Ilya Treyger
(74) *Attorney, Agent, or Firm* — Scott A. Marks; Shumaker & Sieffert, PA

(57) ABSTRACT

In general, the disclosure is directed toward releasing material within a medical device via an optical feedthrough. A system for releasing material with a medical device comprises a cup that holds a material, wherein the cup includes a discharge port, a seal disc that seals the material within the cup, an optical feedthrough assembly coupled to the cup, a shell that defines a chamber within a medical device, wherein the optical feedthrough assembly is coupled to the shell, and a radiant energy source that shines a beam through the optical feedthrough assembly to puncture the seal disc to allow the material to enter the chamber via the discharge port.

18 Claims, 8 Drawing Sheets

OTHER PUBLICATIONS

Notification of Transmittal of the International Search Report and the Written Opinion of the International Searching Authority for patent application No. PCT/US2010/022686, mailed May 7, 2010, 13 pages.

* cited by examiner

RELEASING A MATERIAL WITHIN A MEDICAL DEVICE VIA AN OPTICAL FEEDTHROUGH

TECHNICAL FIELD

The invention relates to medical devices.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other therapeutic agent delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

Manufacturing of medical devices and, in particular, medical devices configured for chronic implantation, may be complex. An outer housing of such implantable medical devices (IMDs) may be hermetically sealed to prevent fluid ingress. Additionally, IMDs may be sterilized prior to implantation within a patient. Since failure of an IMD may require surgical explantation of the IMD, IMDs may also be tested to help ensure that they will function as intended throughout their useful life.

SUMMARY

In general, the disclosure is directed toward releasing material within a medical device via an optical feedthrough. Radiant energy may be transferred across an optical feedthrough embedded in a shell of a medical device chamber. Utilizing radiant energy to release a material within a medical device may simplify the manufacturing process by allowing the loading and release of the material to occur at whatever stage of the manufacturing process is advantageous for improving the medical device's flow through the manufacturing operation.

In one embodiment, the invention is directed to a system comprising a cup that holds a material, wherein the cup includes a discharge port, a seal disc that seals the material within the cup, an optical feedthrough assembly coupled to the cup, a shell that defines a chamber within a medical device, wherein the optical feedthrough assembly is coupled to the shell, and a radiant energy source that shines a beam through the optical feedthrough assembly to puncture the seal disc to allow the material to enter the chamber via the discharge port.

In another embodiment, the invention is directed to a method comprising sealing a material within a cup using a seal disc, wherein the cup includes a discharge port, coupling an optical feedthrough assembly to the cup, coupling the optical feedthrough assembly to a shell that defines a chamber within a medical device, and applying radiant energy through the optical feedthrough assembly to puncture the seal disc to allow the material to enter the chamber via the discharge port.

In another embodiment, the invention is directed to a system comprising means for sealing a material within a cup, wherein the cup comprises a discharge port, means for coupling an optical feedthrough assembly to the cup, means for coupling the optical feedthrough assembly to a shell that defines a chamber within a medical device, and means for applying radiant energy through the optical feedthrough assembly to puncture the means for sealing the material within the cup to allow the material to enter the chamber via the discharge port.

The details of one or more embodiments of the invention are set forth in the accompanying drawings and the description below. Other features, objects, and advantages of the invention will be apparent from the description and drawings, and from the claims.

DETAILED DESCRIPTION

In general, the disclosure is directed toward performing chemical, metallurgical and biological processes inside the one or more compartments that comprise a medical device. These operations include, but are not limited to, melting, cutting, curing, welding, depyrogenation, and the controlled release and/or mixing of materials within a medical device via an optical feedthrough. Radiant energy may be transferred into or out of a chamber of a medical device across an optical feedthrough embedded in a shell of the medical device chamber. Utilizing radiant energy to release a material within a medical device, to connect previously isolated compartments, cure a substance that has been placed inside the medical device, or to depyrogenate surfaces within the medical device, allows the manufacture and test of each of the individual compartments that will ultimately comprise the medical device to proceed independently, and in parallel, rather than sequentially. This provides a more desirable manufacturing flow, reducing lead-time and enabling measurement of many of the medical device's key quality attributes to be performed on the individual compartments, rather than on the final medical device. Since the measurement of major quality characteristics is performed earlier, on less expensive components, scrap costs are reduced.

Figure 1:
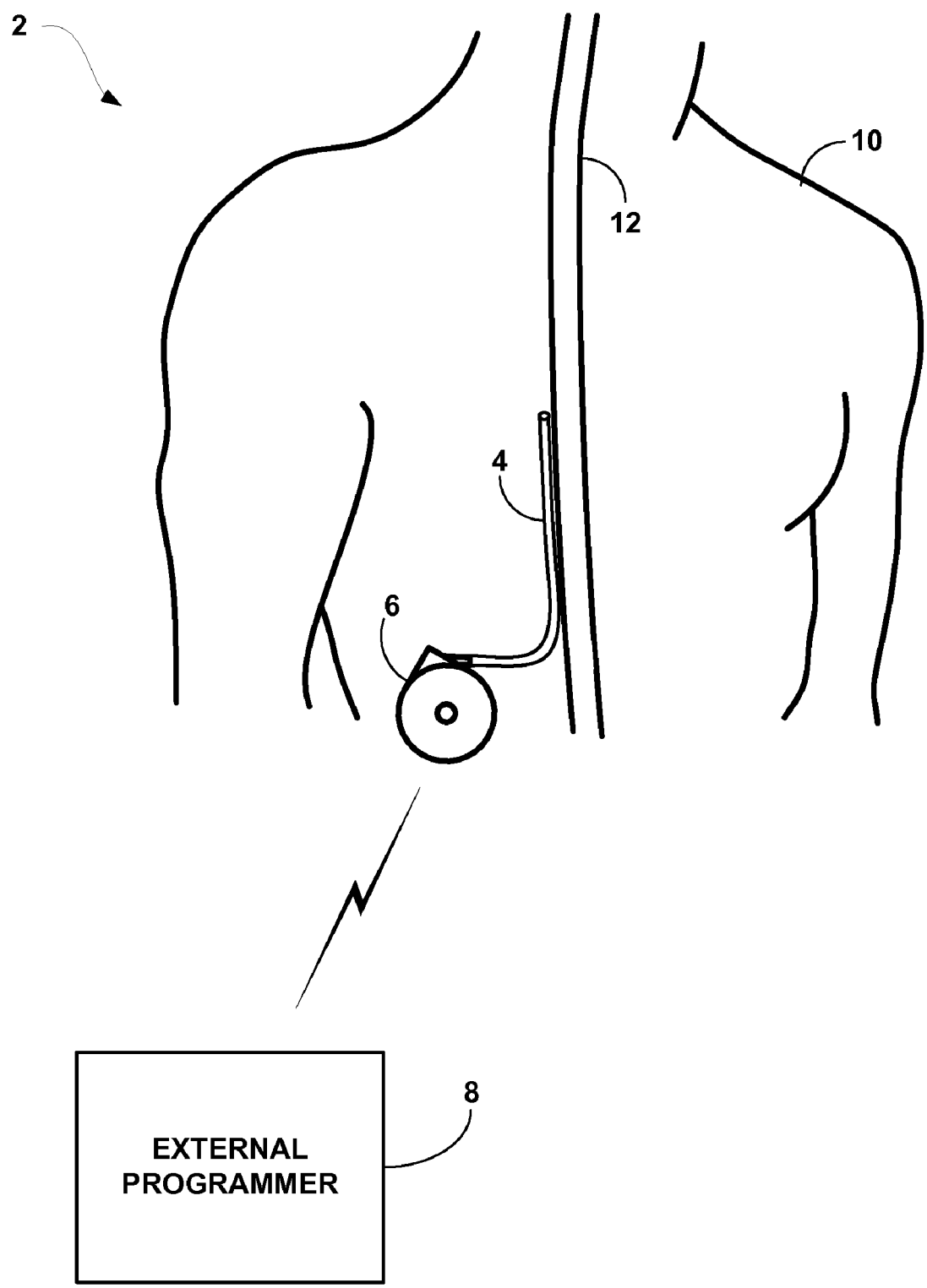
FIG. 1 is a conceptual diagram illustrating an implantable therapeutic agent delivery system including a delivery catheter.

FIG. 1 is a conceptual diagram illustrating an implantable medical device (IMD) system 2 including a delivery catheter 4 coupled to IMD 6. In the example illustrated in FIG. 1, IMD 6 is an implantable therapeutic agent delivery device and, therefore, implantable medical device system 2 may be referred to as implantable therapeutic agent delivery system 2. Although the techniques described in this disclosure may be generally applicable to a variety of medical devices including external and implantable medical devices, application of such techniques to IMDs and, more particularly, implantable therapeutic agent delivery devices will be described for purposes of illustration. The disclosure will refer to an implantable therapeutic agent delivery system for purposes of illustration, but without limitation as to other types of medical devices.

The techniques described in this disclosure may be generally applicable to a variety of medical devices including external and implantable medical devices. For example, techniques described in this disclosure may be applicable to a therapeutic agent delivery device configured to deliver a drug or other therapeutic agent to a patient, e.g., via one or more catheters. As another example, techniques described in this disclosure may be applicable to an electrical stimulator configured to deliver electrical stimulation therapy to a patient via one or more stimulation electrodes. Examples medical devices, such as therapy therapeutic agent delivery devices and electrical stimulators, are described in further detail in U.S. Provisional Patent Application No. 61/080,089 to Skelton et al., which was filed on Jul. 11, 2008 is entitled "POSTURE STATE MANAGEMENT FOR POSTURE-RESPONSIVE THERAPY," and is incorporated herein by reference in its entirety. The techniques described in this disclosure may also be applicable to non-medical devices, such as nanodevices and/or devices with one or more sterile components. Application of the techniques of this disclosure to implantable medical devices (IMDs), e.g., IMD 6, will be described for purposes of illustration, but without limitation as to other types of medical or non-medical devices.

As shown in FIG. 1, system 2 includes an IMD 6 and external programmer 8 shown in conjunction with a patient 10. In the example of FIG. 1, IMD 6 is an implantable therapeutic agent delivery device configured to deliver a therapeutic agent proximate to spinal cord 12 of patient 10, e.g., for relief of chronic pain or other symptoms. Example therapeutic agents include, but are not limited to, pharmaceutical agents, insulin, pain relieving agents, anti-inflammatory agents, gene therapy agents, or the like. A therapeutic agent is delivered from IMD 6 to spinal cord 12 of patient 10 via one or more outlets of catheter 4. Although FIG. 1 is directed to deliver a therapeutic agent to spinal cord 12, system 2 may alternatively be directed to any other condition that may benefit from the delivery of a therapeutic agent. In addition, patient 10 is ordinarily a human patient.

IMD 6 may operate using parameters that define the method of therapeutic agent delivery. IMD 6 may include programs, or groups of programs, that define different delivery methods for patient 10. For example, a program that controls delivery of a drug or other therapeutic agent may include a titration rate or information controlling the timing of bolus deliveries. Patient 10 may use external programmer 8 to adjust the programs or groups of programs to regulate the therapy delivery.

In the example of FIG. 1, catheter 4 includes one or more infusion outlets that are placed adjacent to the target tissue of spinal cord 12. One or more infusion outlets may be disposed at a distal tip of a catheter 4 and/or at other positions at intermediate points along catheter 4. Catheter 4 may be implanted and coupled to IMD 6. Alternatively, catheter 4 may be implanted and coupled to an external stimulator, e.g., through a percutaneous port. In some cases, an external device may be used on a temporary basis to evaluate potential efficacy to aid in consideration of chronic implantation for a patient.

IMD 6 may deliver a therapeutic agent to a target tissue via catheter 4. In the example illustrated by FIG. 1, the target tissue is spinal cord 12. Delivery of a therapeutic agent to spinal cord 12 may, for example, prevent pain signals from traveling through the spinal cord and to the brain of the patient. Patient 10 may perceive the interruption of pain signals as a reduction in pain and, therefore, efficacious therapy may result. In other examples, IMD 6 may deliver a therapeutic agent to other target tissue sites, such as nerves, smooth muscle, and skeletal muscle.

A user, such as a clinician or patient 10, may interact with a user interface of external programmer 8 to program IMD 6. Programming of IMD 6 may refer generally to the generation and transfer of commands, programs, or other information to control the operation of IMD 6. For example, external programmer 8 may transmit programs, parameter adjustments, program selections, group selections, or other information to control the operation of IMD 6, e.g., by wireless telemetry. As one example, a user may select programs or program groups. Again, a program that controls delivery of a drug or other therapeutic agent may include a titration rate or information controlling the timing of bolus deliveries. A group may be characterized by multiple programs that are delivered simultaneously or on an interleaved or rotating basis.

In some cases, external programmer 8 may be characterized as a physician or clinician programmer if it is primarily intended for use by a physician or clinician. In other cases, external programmer 8 may be characterized as a patient programmer if it is primarily intended for use by a patient. A patient programmer is generally accessible to patient 10 and, in many cases, may be a portable device that may accompany the patient throughout the patient's daily routine. In general, a physician or clinician programmer may support selection and generation of programs by a clinician for use by IMD 6, whereas a patient programmer may support adjustment and selection of such programs by a patient during ordinary use.

IMD 6 may be constructed with a biocompatible housing, such as titanium or stainless steel, or a polymeric material such as silicone or polyurethane, and surgically implanted at a site in patient 10 near the pelvis. IMD 6 may also be implanted in patient 10 at a location minimally noticeable to patient 10. Alternatively, IMD 6 may be external with one or more percutaneously implanted catheters. For delivery of a therapeutic agent to spinal cord 12, IMD 6 may be located in the lower abdomen, lower back, upper buttocks, or other location to secure IMD 6. Catheter 4 may be tunneled from IMD 6 through tissue to reach the target tissue adjacent to spinal cord 12 for therapeutic agent delivery. In addition, IMD 6 may be refillable to allow chronic therapeutic agent delivery.

Although IMD 6 is shown as coupled to only one catheter 4 positioned along spinal cord 12, additional catheters may also be coupled to IMD 6. Multiple catheters may deliver drugs or other therapeutic agents to the same anatomical location or the same tissue or organ. Alternatively, each catheter may deliver therapy to different tissues within patient 10 for the purpose of treating multiple symptoms or conditions. In some embodiments, IMD 6 may be an external device which includes a percutaneous catheter that forms catheter 4 or that is coupled to catheter 4, e.g., via a fluid coupler.

In some examples, IMD 6 may comprise an electrical stimulator. An electrical stimulator may perform therapy functions similar to a therapeutic agent delivery device via delivery of electrical stimulation therapy instead of therapeutic agent stimulation therapy. In examples in which IMD 6 is an electrical stimulator, catheter 4 may include one or more stimulation electrodes (not shown in FIG. 1) and the parameters for a program that controls delivery of stimulation therapy by IMD 6 may include information identifying which electrodes have been selected for delivery of stimulation according to a stimulation program and the polarities of the selected electrodes.

A program that controls delivery of electrical stimulation by IMD 6 may also include a voltage or current amplitude. Electrical stimulation delivered by IMD 6 may take the form of electrical stimulation pulses or continuous stimulation waveforms. In examples in which IMD 6 delivers stimulation pulses, a stimulation program may also define a pulse width and pulse rate. Electrical stimulation may be used to treat tremor, Parkinson's disease, epilepsy, urinary or fecal incontinence, sexual dysfunction, obesity, or gastroparesis. In this manner, IMD 6 may be configured to provide therapy taking the form of deep brain stimulation (DBS), pelvic floor stimulation, gastric stimulation, or any other stimulation therapy. In other embodiments, IMD 6 may be capable of performing both therapeutic agent delivery and electrical stimulation therapy.

Figure 2:
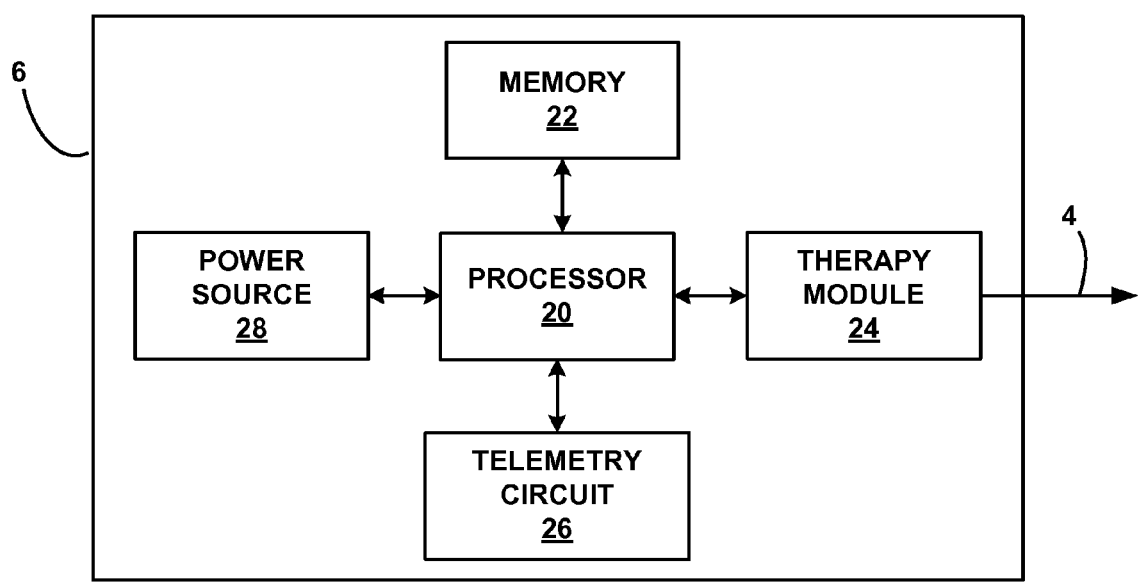
FIG. 2 is a functional block diagram illustrating various components of the implantable therapeutic agent delivery device of FIG. 1.

FIG. 2 is a functional block diagram illustrating various components of an IMD 6. In the example of FIG. 2, IMD 6 includes a processor 20, memory 22, therapy module 24, telemetry circuit 26, and power source 28. Memory 22 may store instructions for execution by processor 20, therapy data, and any other information regarding therapy or patient 10. Therapy information may be recorded for long-term storage and retrieval by a user, and the therapy information may include any data created by or stored in IMD 6. Memory 22 may include separate memories for storing instructions, program histories, and any other data that may benefit from separate physical memory modules.

Processor 20 controls therapy module 24 to deliver therapeutic agent and/or electrical stimulation via catheter 4 according to therapy instructions stored within memory 22. Components described as processors within IMD 6, external programmer 8 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Processor 20 may access locations in memory 22 to retrieve therapy parameters for a program and control therapy module 24 to deliver therapy via the indicated program parameters. Therapy module 24, e.g., under control of processor 20, then makes use of the therapy parameters in delivering the therapeutic agent and/or electrical stimulation to patient 10. Processor 20 also may control telemetry circuit 26 to send and receive information to and from external programmer 8.

In examples in which IMD 6 is configured to deliver a therapeutic agent to patient 10, therapy module 24 may include a reservoir to hold the therapeutic agent and a pump mechanism to force the therapeutic agent out of catheter 4 and into patient 10. Memory 22 may contain programs or groups of programs that define the therapeutic agent delivery therapy for patient 10, and processor 20 may control therapy module 24 according to therapy instructions stored within memory 22. A program may indicate the bolus size or flow rate of the therapeutic agent, and processor 20 may control therapy delivery accordingly.

In examples in which IMD 6 is configured to deliver electrical stimulation, therapy module 24 may include stimulation generation circuitry to generate stimulation pulses or waveforms and switching circuitry to switch the stimulation across different electrode combinations, e.g., in response to control by processor 20. In particular, processor 20 may control the switching circuitry on a selective basis to cause therapy module 24 to deliver electrical stimulation to selected electrode combinations. In other embodiments, therapy module 24 may include multiple current or voltage sources to drive more than one electrode combination at one time. Memory 22 may contain programs or groups of programs that define the electrical stimulation therapy for patient 10, and processor 20 may control therapy module 24 according to therapy instructions stored within memory 22. A program may indicate an electrode combination, the polarities of the selected electrodes, and a voltage or current amplitude. When electrical stimulation pulses are delivered, a program may also include a pulse width and pulse rate.

Telemetry module 24 includes any suitable hardware, firmware, software or any combination thereof for communicating with another device, such as external programmer 8. Under the control of processor 20, telemetry module 24 may receive downlink telemetry from and send uplink telemetry to programmer 8 with the aid of an antenna, which may be internal and/or external. Processor 20 may provide the data to be uplinked to programmer 8 and the control signals for the telemetry circuit within telemetry module 24, e.g., via an address/data bus. In some examples, telemetry module 24 may provide received data to processor 20 via a multiplexer.

Wireless telemetry between IMD 6 and external programmer 8 may be accomplished by radio frequency (RF) communication or proximal inductive interaction of IMD 6 with external programmer 8. Telemetry circuit 26 may send information to and receive information from external programmer 8 on a continuous basis, at periodic intervals, at non-periodic intervals, or upon request from IMD 6 or programmer 8. To support RF communication, telemetry circuit 26 may include appropriate electronic components, such as amplifiers, filters, mixers, encoders, decoders, and the like.

The various components of IMD 6 are coupled to power source 28, which may include a rechargeable or non-rechargeable battery or a supercapacitor. A non-rechargeable battery may be selected to last for several years, while a rechargeable battery may be inductively charged from an external device, e.g., on a daily or weekly basis.

Figure 3:
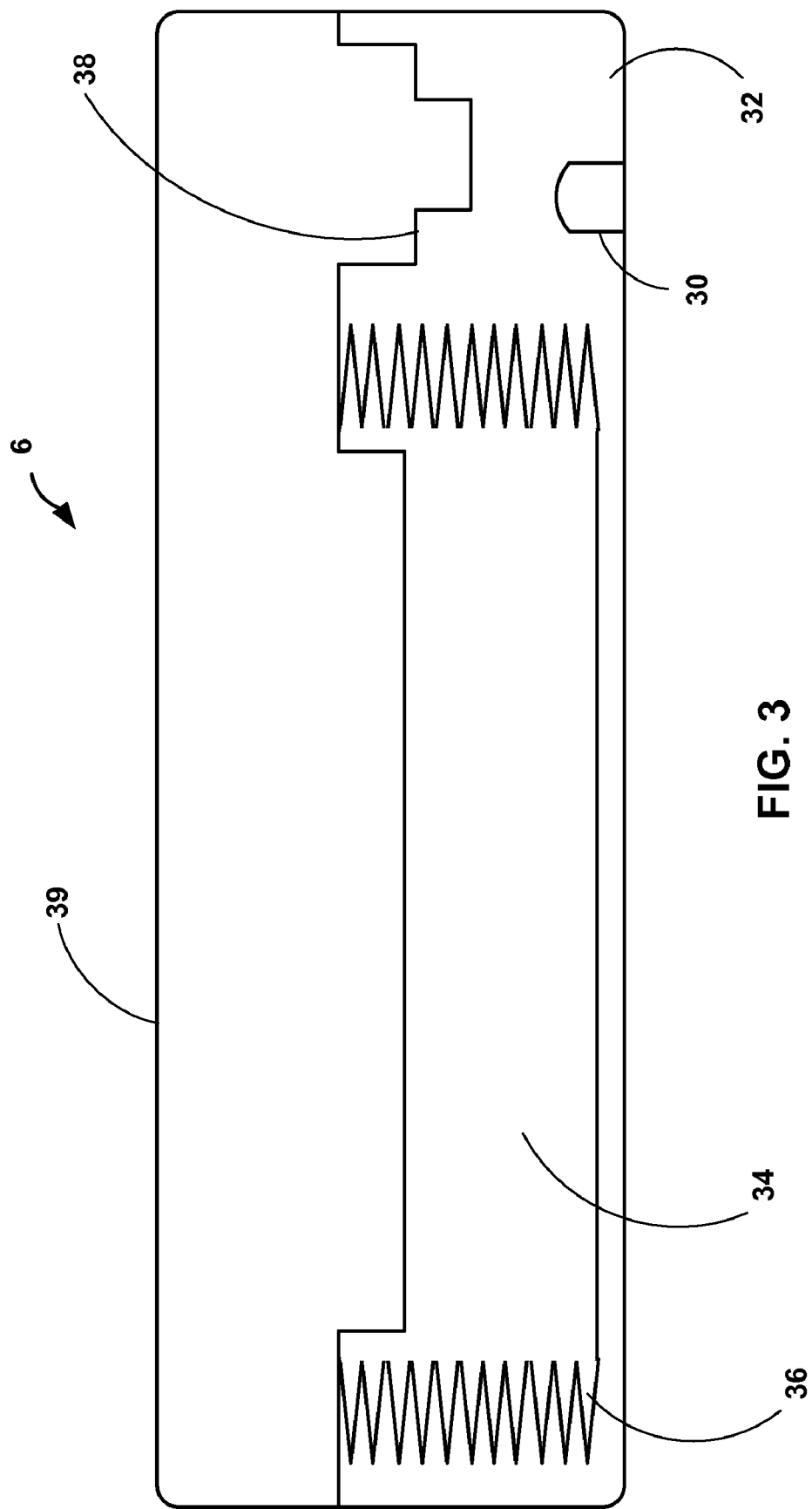
FIG. 3 is a conceptual diagram illustrating a cross-sectional view of a propellant release assembly and propellant chamber of the implantable therapeutic agent delivery device of FIG. 1.

FIG. 3 is a conceptual diagram illustrating a cross-sectional view of material release assembly 30 and chamber 32 of implantable therapeutic agent delivery device 6. In the example illustrated in FIG. 3, material release assembly 30 is configured to release propellant into chamber 32 of implantable therapeutic agent delivery device 6. Although the techniques described in this disclosure may be generally applicable to a release of any suitable material within a medical device, propellant release is described herein as one example application of releasing a material within a medical device, but without limitation as to other types of materials that may be released.

IMD 6 includes reservoir 34 configured to hold a therapeutic agent. Reservoir 34 is expandable and includes bellows 36 that aid in allowing reservoir 34 to expand. Reservoir 34 is enclosed within chamber 32. In the illustrated example, chamber 32 is configured to hold a propellant. Material release assembly 30 may release a specific volume of propellant into chamber 32. For example, material release assembly 30 may be filled with a measured amount of propellant for release into chamber 32. Once released into chamber 32, the propellant, e.g., in the form of gas, exerts pressure on reservoir 34. The pressure may aid in driving the therapeutic agent from reservoir 34 to a pump mechanism of therapy module 22 (FIG. 3), which dispenses the therapeutic agent based on therapy parameters values of a selected program, e.g., at a rate defined by a selected program. The pressure that the propellant exerts on reservoir 34 may allow reservoir 34 to fully compress.

Chamber 32 may be enclosed within shell 38. More specifically, shell 38 defines chamber 32 such that once material release assembly 30 releases the propellant into chamber 32, the propellant is confined within the boundaries of shell 38. In the example illustrated in FIG. 3, outer housing 39 of IMD 6 defines a portion of shell 38, and material release assembly 30 is embedded in the portion of housing 39 that defines a portion of shell 38. As described with further detail with respect to FIGS. 4 and 5, material release assembly 30 may be partially embedded within shell 38 such that an outer surface of material release assembly 30 remains uncovered.

Although material release assembly 30 is coupled to an outer housing 39 of IMD 6 in the example of propellant release illustrated in the FIGS. 3, in other examples material release assembly 30 may be coupled to other portions of shell 38 or any other shell that defines a chamber within IMD 6. In general, material release assembly 30 may be coupled to a portion of a shell that defines a chamber within IMD 6 to facilitate release of a material within the chamber. A shell that defines a chamber does not necessarily include a portion of outer housing 39 of IMD 6. For example, IMD 6 may include one or more shells that are fully enclosed within housing 39, and each of the shells may define a chamber within IMD 6.

Figure 4:
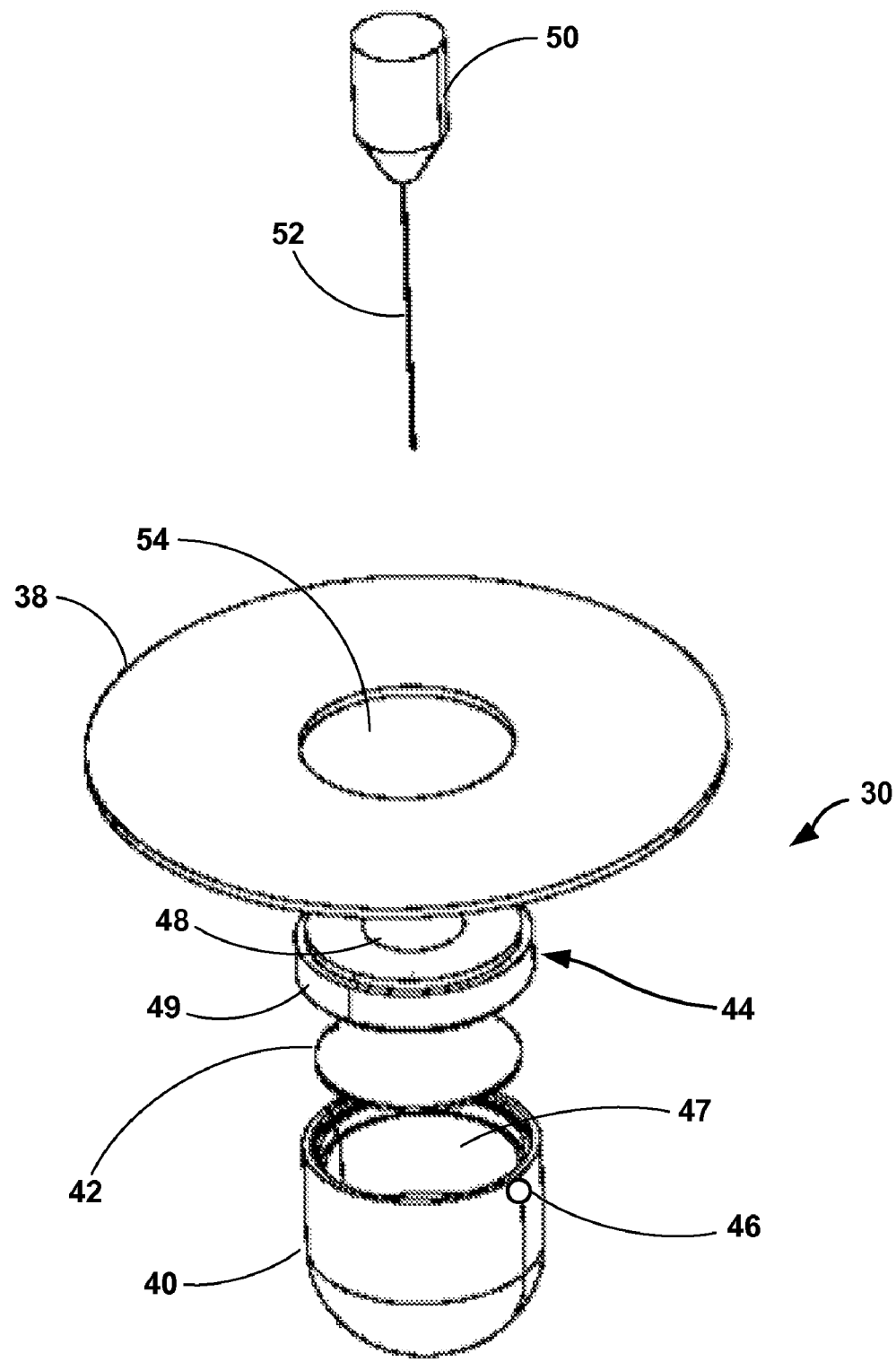
FIG. 4 is a conceptual diagram illustrating a perspective view of various components of the material release assembly of FIG. 3.

FIG. 4 is a conceptual diagram illustrating a perspective view of various components of material release assembly 30. Material release assembly 30 comprises cup 40, seal disc 42, and optical feedthrough assembly 44. Cup 40 is configured to hold the material intended from release into chamber 32 (FIG. 3) defined by shell 38. Cup 40 may take the form of any shape and is not limited to the shape of cup 40 illustrated in FIG. 4. The material may be inserted into cup 40 and seal disc 42 may be coupled to cup 40 to seal the material within cup 40. Cup 40 may be filled with a measured amount of material to allow material release assembly 30 to release a specific amount of material into chamber 32. In general, the material may be a gas.

Cup 40 includes discharge port 46, which may take the form of a hole in cup 40. In order to seal the material within cup 40, sealing disc 42 may couple to cup 40 such that the material is prohibited from escaping from both discharge port 46 and the opening 47 of cup 40. For example, seal disc 42 may be coupled to cup 40 at a location between the material and discharge port 46. The coupling between cup 40 and seal disc 42 is described with further detail with respect to FIG. 6.

Optical feedthrough assembly 44 includes optical window 48. Optical window 48 may be configured to allow radiant energy to pass through. For example, optical window 48 may be transparent. The shape and material composition of optical window 48 may be selected based on the desired optical characteristics of optical window 48. Optical window 48 may, for example, be constructed of glass, sapphire, polymer, and/or crystalline material. For example, optical window 48 may be constructed of single-crystal sapphire or thermal shock resistant borosilicate glass. Optical feedthrough assembly 44 may also comprise ferrule fitting 49. Ferrule fitting 49 may be sized, shaped, and/or otherwise configured to allow optical feedthrough assembly 44 to be coupled to cup 40.

Optical feedthrough assembly 44 may be configured to fit within an aperture defined by shell 38 of cavity 32 (FIG. 3). A portion of shell 38 is shown in FIG. 4 for purposes of illustration. In the example illustrated in FIG. 4, shell 38 defines aperture 54 that may be configured to accept optical feedthrough assembly 44.

Figure 5:
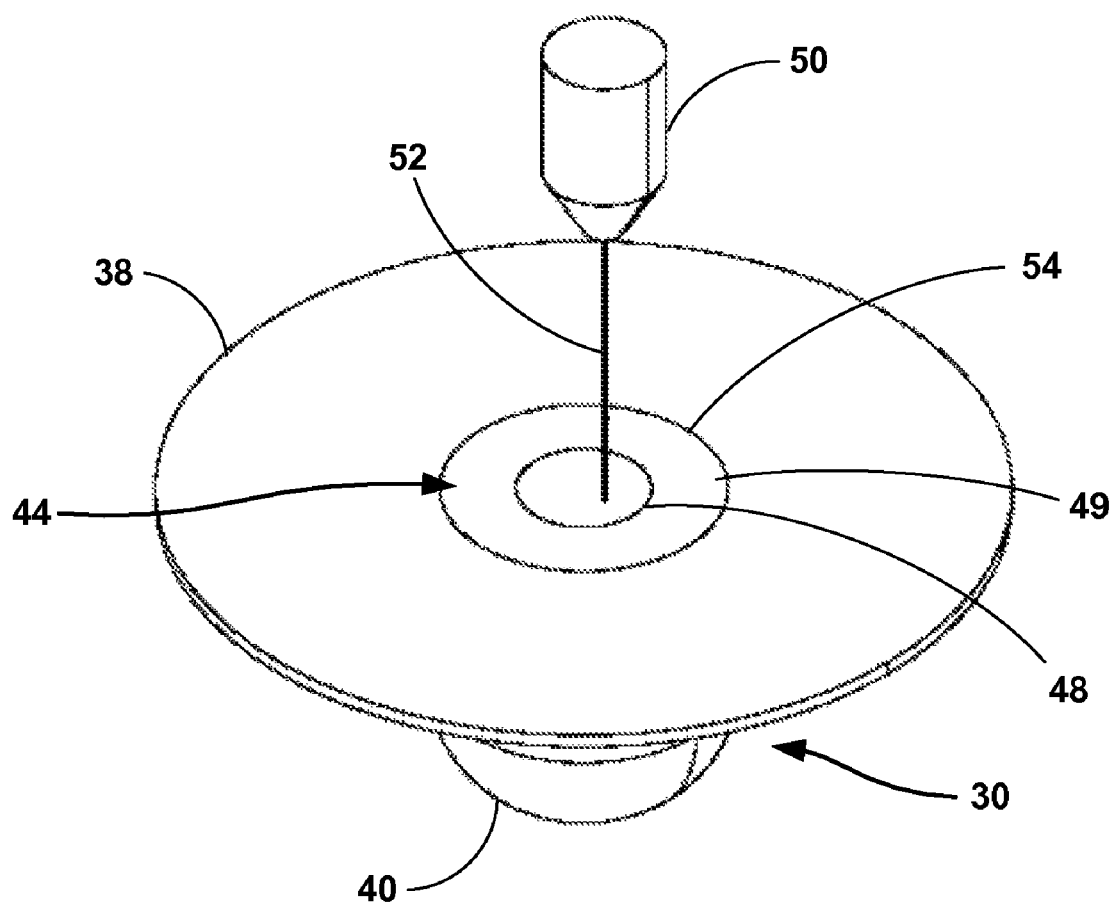
FIG. 5 is a conceptual diagram illustrating a perspective view of the material release assembly of FIG. 4 inserted within an aperture defined by a shell of a medical device chamber.

FIG. 5 is a conceptual diagram illustrating a perspective view of material release assembly 30 coupled to shell 38 such that optical feedthrough assembly 44 remains uncovered by shell 38. Optical feedthrough assembly 44 may be welded or otherwise coupled to shell 38. As one example, optical feedthrough assembly 44 may be welded to shell 38 around the perimeter of aperture 54.

In some examples in which outer housing 39 (FIG. 3) of IMD 6 forms a portion of the shell 38 of chamber 32 (FIG. 3), optical feedthrough assembly 44 may be coupled to housing 39. In such examples, aperture 54 may comprise an aperture of housing 39. In examples in which IMD 6 is configured for implantation within patient 10 (FIG. 1), housing 39 of IMD 6 may be constructed of biocompatible materials, such as titanium or stainless steel, or a polymeric material such as silicone or polyurethane. Housing 39 may also be hermetically sealed to prevent fluid ingress. In such examples, the interface between optical feedthrough assembly 44 and housing 39 may be hermetically sealed, e.g., using biocompatible materials.

As illustrated in FIGS. 4 and 5, radiant energy source 50, e.g., laser 50, may shine beam 52 through optical window 48 and onto seal disc 42. As described in further detail with respect to FIG. 6, beam 52 may puncture a hole in seal disc 42 to allow the material to escape from cup 40 to chamber 32 (FIG. 3). By coupling material release assembly 30 to shell 38 of chamber 32, the material may be released into chamber 32 after chamber 32 has been fully sealed. Additionally, if material release assembly 30 is coupled to an outer housing 39 (FIG. 3) of IMD 6, the material may be released into chamber 32 after the entire IMD 6 has been fully assembled and sealed. Therefore, material release assembly 30 may allow a material to be released into chamber 32 at a later stage in the manufacturing process.

Figure 6:
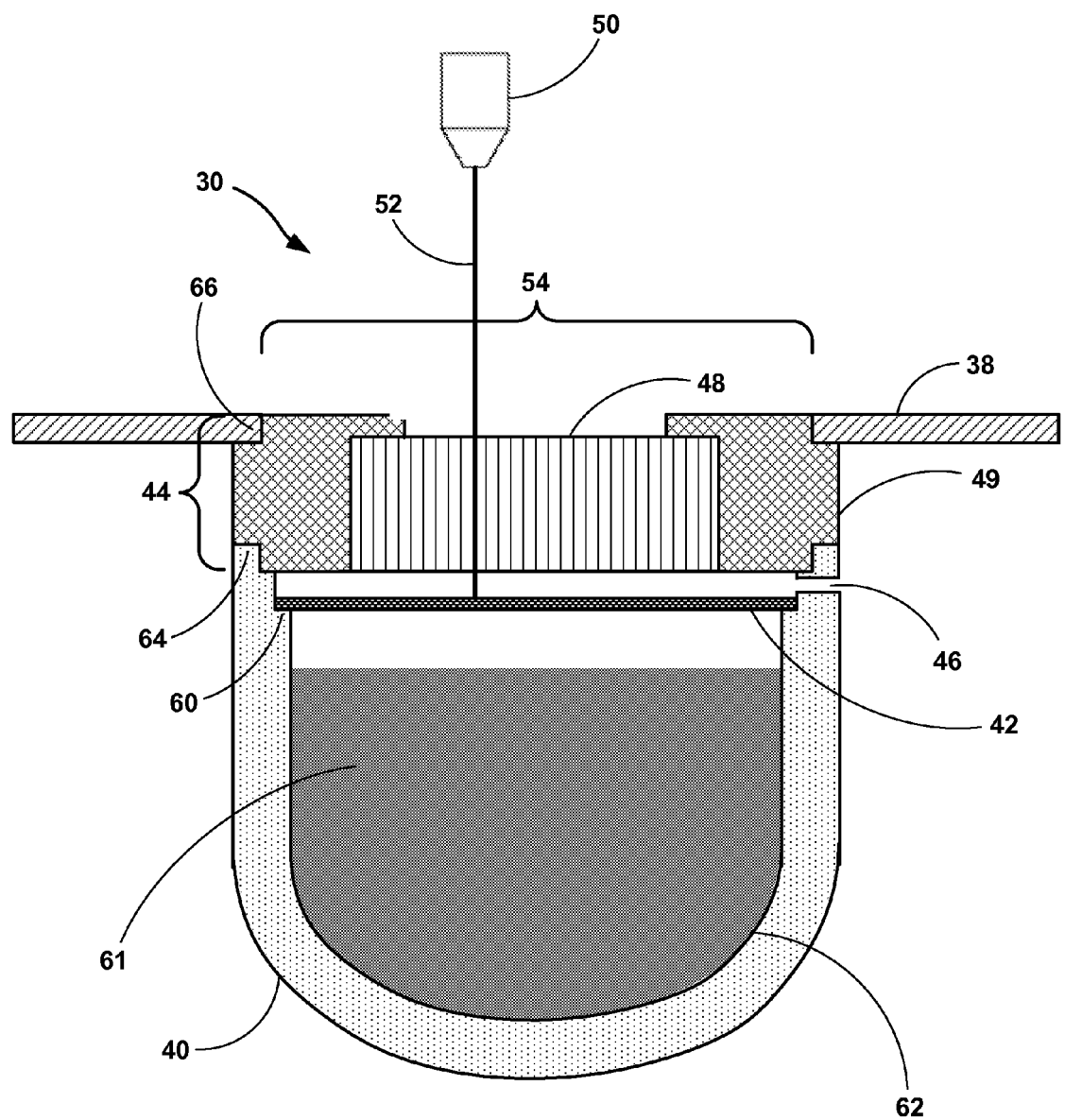
FIG. 6 is a conceptual diagram illustrating a cross-sectional view of the material release assembly of FIG. 4.

FIG. 6 is a conceptual diagram illustrating a cross-sectional view of material release assembly 30. Seal disc 42 may seal the material within cup 40. For example, cup 40 may define a lip 60 that accepts seal disc 42. After seal disc 42 is placed on lip 60 of cup 40, seal disc 42 may be welded to cup 40. For example, welding may occur around the circumference of seal disc 42 where seal disc 42 joins cup 40. One or both of cup 40 and seal disc 42 may be constructed of titanium and/or other metals to facilitate welding. In this manner, seal disc 42 may enclose a material, e.g., material 61, within cavity 62 of cup 40 and prevent the material from escaping from discharge port 46. In some examples, cup 40 may be filled with a measured amount of material to allow material release assembly 30 to release a specific amount of material into chamber 32 (FIG. 3).

Cup 40 may also define a lip 64 that mates with a lower lip of optical feedthrough assembly 44, and once optical feedthrough assembly 44 is placed on lip 64, optical feedthrough assembly 44 may be welded to cup 40. For example, welding may occur around the circumference of optical feedthrough assembly 44 where optical feedthrough assembly 44 joins cup 40. Although welding is described as an example means for coupling cup 40 to seal disc 42 and optical feedthrough assembly 44, other systems and techniques for coupling elements together may be utilized. For example, cup 40 may be coupled to seal disc 42 and/or optical feedthrough assembly 44 via an adhesive, such as an epoxy.

Optical feedthough assembly 44 may also define an upper lip 66. Upper lip 66 may mate with aperture 54 of shell 38. For example, aperture 54 may be configured to abut against upper lip 66 of optical feedthrough assembly 44. Once optical feedthrough assembly 44 is placed within aperture 54 of shell 38, optical feedthrough assembly 44 and shell 38 may be coupled together.

In examples in which aperture 54 comprises an aperture of the outer housing 39 (FIG. 3) of IMD 6 and IMD 6 is configured for implantation within patient 10, the interface between optical feedthrough assembly 44 and housing 39 may be hermetically sealed. As one example, optical feedthrough assembly 44 may be welded to housing 39 around the perimeter of aperture 54, e.g., where optical feedthrough assembly 44 joins housing 39, to create a hermetic seal.

Once material release assembly 30 has been assembled and coupled to shell 38, beam 52 may shine through optical window 48 and onto seal disc 42. Beam 52 may puncture a hole in seal disc 42 to allow the material within cavity 62 to escape from cup 40 via discharge port 46. Since discharge port 46 is enclosed within shell 38 of chamber 32 (FIG. 3), the material transfers from cup 40 to chamber 32 via discharge port 46. By coupling material release assembly 30 to shell 38 of chamber 32, the material may be released into chamber 32 after chamber 32 has been fully sealed. Additionally, if material release assembly 30 is coupled to an outer housing 39 (FIG. 3) of IMD 6, the material may be released into chamber 32 after the entire IMD 6 has been fully assembled and sealed. Therefore, material release assembly 30 may allow the material to be released into chamber 32 at a later stage in the manufacturing process.

In some examples, IMD 6 may include a plurality of material release assemblies 30 to facilitate release of one or more materials into the same or different chambers within IMD 6. For example, IMD 6 may include two material release assemblies 30 that release the same or different material into two different chambers. As another example, IMD 6 may include a plurality of material release assemblies 30 that release different materials into one chamber. Once released the different materials may mix within the chamber. This may be particularly useful when reducing exposure to the mixed materials is desirable, e.g., when a mixture of the released materials is hazardous. Additionally, each of the plurality of material release assemblies 30 may be filled with a measured amount of material such that the chamber receives a controlled composition of the material mixture. By controlling the amount of material inserted into each material release assembly 30, the mixing ratio may be controlled.

Figure 7:
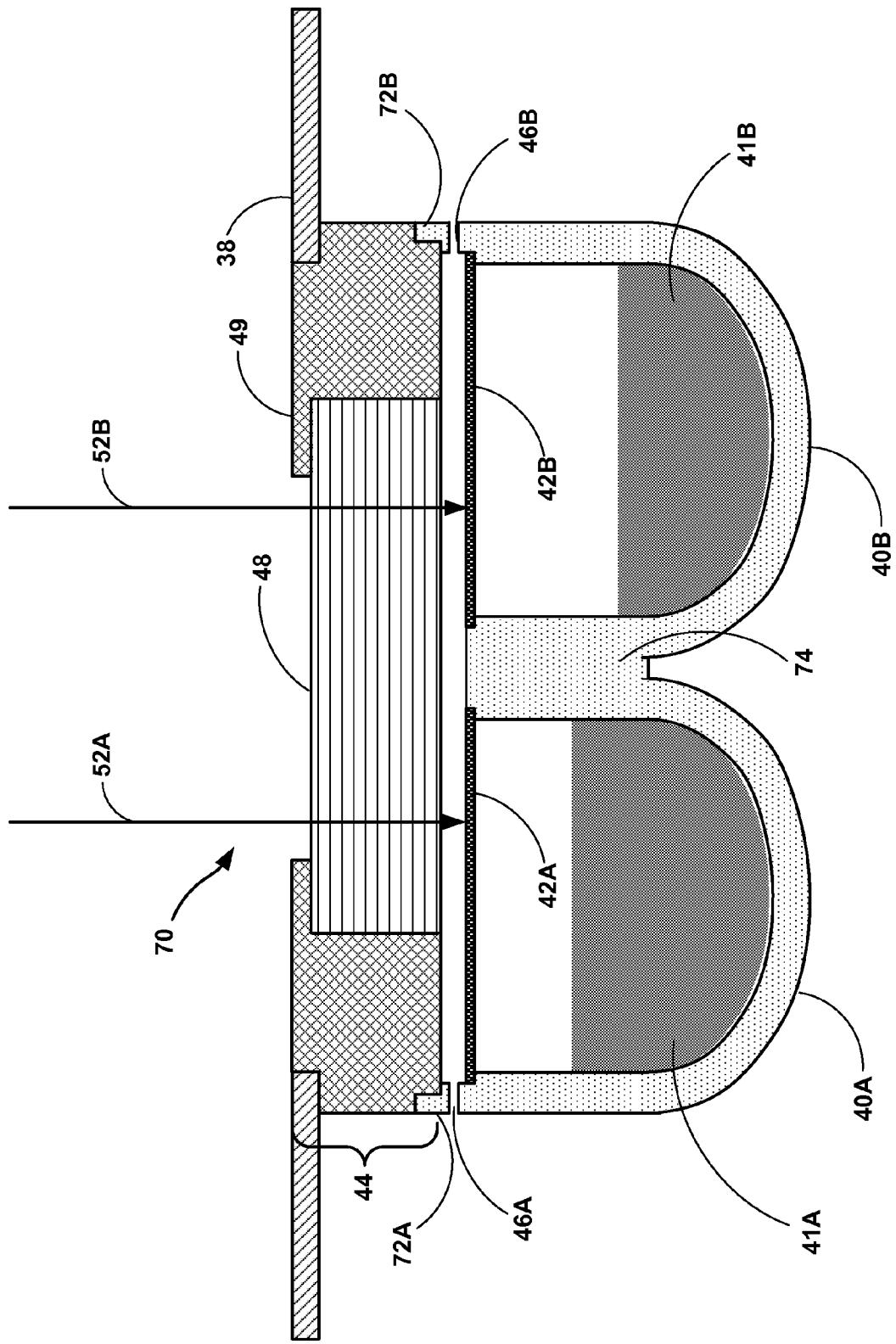
FIG. 7 is a conceptual diagram illustrating a cross-sectional view of a material release assembly that includes two individually sealed cups.

Additionally or alternatively, one optical feedthrough assembly 44 may allow access to multiple cups 40 that are individually sealed with respective seal discs 42. FIG. 7 is a conceptual diagram illustrating a cross-sectional view of material release assembly 70 that includes two individually sealed cups 40A and 40B. Cups 40A and 40B may take the form of any shape and are not limited to the shape of cups 40A and 40B illustrated in FIG. 7.

Material release assembly comprises cups 40A and 40B, sealing discs 42A and 42B, discharge ports 46A and 46B, and optical feedthrough assembly 44. Cups 40A and 40B may each hold a material, e.g., materials 41A and 41B respectively, for release into chamber 32 (FIG. 3). Cups 40A and 40B may be individually sealed by seal discs 42A and 42B, respectively. A measured amount of material may be sealed within each of cups 40A and 40B. Cups 40A and 40B may hold the same or different material as well as the same or different amounts of material.

Cups 40A and 40B may be coupled to optical feedthrough assembly 44. For example, cup 40A may be coupled to optical feedthrough assembly 44 at outer edge 72A and cup 40B may be coupled to optical feedthrough assembly 44 at outer edge 72B. In the illustrated example, cups 40A and 40B are joined at their interface 74. In other examples, cups 40A and 40B may be unjoined. Optical feedthrough assembly 44 is coupled to shell 38, as described with respect to FIG. 6.

Beams 52A and 52B of radiant energy may shine through optical window 48 of optical feedthrough assembly 44 to puncture seal discs 42A and 42B, respectively. Puncturing seal discs 42A and 42B allows the materials held in cups 40A and 40B to enter chamber 32 (FIG. 3) via discharge ports 46A and 46B. Two discharge ports 46A and 46B are illustrated in FIG. 7 for purposes of example. In other examples, the materials from cups 40A and 40B may enter chamber 32 via the same discharge port.

Figure 8:
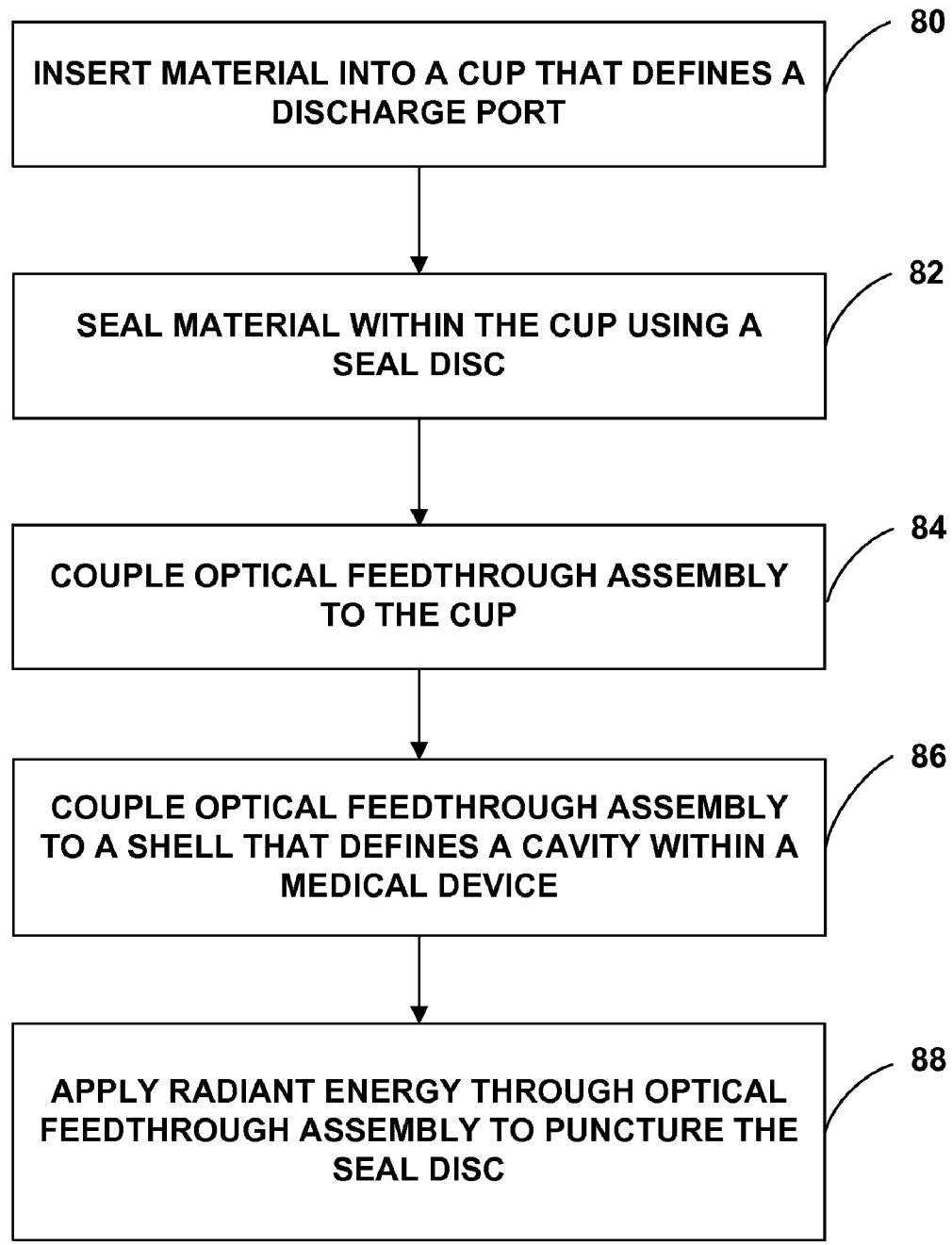
FIG. 8 is a flow diagram illustrating an example technique for releasing a material within a medical device.

FIG. 8 is a flow diagram illustrating an example technique for releasing a material within IMD 6. Although the technique illustrated in FIG. 8 is described with respect to the example of material release assembly 30 illustrated in FIG. 6, techniques for releasing a material within a medical device are applicable to other embodiments of material release assemblies. First, a material is inserted into cup 40, which defines discharge port 46 (80). Cup 40 may be filled with a measured amount of material to allow material release assembly 30 to release a specific amount of material into chamber 32 (FIG. 3). After the material is inserted into cup 40, the material is sealed within cup 40 using seal disc 42 (82). For example, seal disc 42 may be inserted into cup 40 such that seal disc 42 abuts lip 60 of cup 40. Once inserted, seal disc 42 may be coupled to cup 40 to seal the material within cup 40. For example, seal disc 42 may be welded to cup 40 about the circumference of seal disc 42. In general, seal disc 42 may be positioned between the material and discharge port 46 to prevent the material from escaping from discharge port 46.

After the material is sealed within cup 40, optical feedthrough assembly 44 is coupled to cup 40 (84). Cup 40 may include lip 64 configured to mate with a lower lip of optical feedthrough assembly 44 to aid in coupling cup 40 and optical feedthrough assembly 44. As one example, optical feedthrough assembly 44 may be welded to cup 40 around the circumference of optical feedthrough assembly 44 where optical feedthrough assembly 44 joins cup 40.

Optical feedthrough assembly 44 may be coupled to shell 38 that defines cavity 32 within IMD 6 (86). Optical feedthough assembly 44 may define an upper lip 66 that mates with aperture 54 of shell 38 to facilitate coupling optical feedthrough assembly 44 to shell 38. For example, aperture 54 may be configured to abut against upper lip 66 of optical feedthrough assembly 44.

In examples in which aperture 54 comprises an aperture of the outer housing 39 (FIG. 3) of IMD 6 and IMD 6 is configured for implantation within patient 10, the interface between optical feedthrough assembly 44 and housing 39 may be hermetically sealed. As one example, optical feedthrough assembly 44 may be welded to housing 39 around the perimeter of aperture 54, e.g., where optical feedthrough assembly 44 joins housing 39, to create a hermetic seal.

Once material release assembly 30 has been assembled and coupled to shell 38, radiant energy, e.g., in the form of beam 52 (FIG. 4), is applied through optical feedthrough assembly 44 to puncture seal disc 42 (88). Puncturing seal disc 42 allows the material within cup 40 to escape via discharge port 46. Since discharge port 46 is enclosed within shell 38 of chamber 32 (FIG. 3), the material transfers from cup 40 to chamber 32 via discharge port 46. By coupling material release assembly 30 to shell 38 of chamber 32, the material may be released into chamber 32 after chamber 32 has been fully sealed. Additionally, if material release assembly 30 is coupled to an outer housing 39 (FIG. 3) of IMD 6, the material may be released into chamber 32 after the entire IMD 6 has been fully assembled and sealed. Therefore, material release assembly 30 may allow a material to be released into chamber 32 at a later stage in the manufacturing process.

Various embodiments of the invention have been described. These and other embodiments are within the scope of the following claims.

The invention claimed is:

1. A system comprising:
a cup that holds a material, wherein the cup includes a discharge port;
a seal disc that seals the material within the cup;
an optical feedthrough assembly coupled to the cup;
a shell that defines a chamber within a medical device, wherein the optical feedthrough assembly is coupled to the shell; and
a radiant energy source that shines a beam through the optical feedthrough assembly to puncture the seal disc to allow the material to enter the chamber via the discharge port.

2. The system of claim 1, wherein the material comprises a propellant, the chamber comprises a propellant chamber, and the medical device comprises a therapeutic agent delivery device.

3. The system of claim 1, wherein the shell comprises at least a portion of an outer housing of the medical device.

4. The system of claim 3, wherein the optical feedthrough assembly is coupled to the outer housing of the medical device, and wherein an interface between the outer housing and the optical feedthrough assembly is hermetically sealed.

5. The system of claim 1, wherein the medical device comprises an implantable medical device.

6. The system of claim 1, wherein the medical device comprises a therapeutic agent delivery device.

7. The system of claim 1, wherein the optical feedthrough assembly comprises an optical window that allows the beam through the optical feedthrough assembly.

8. The system of claim 7, wherein the optical window comprises at least one of glass, sapphire, polymer, or a crystalline material.

9. The system of claim 7, wherein the cup comprises a lip configured to accept the sealing disc, and the sealing disc seals the material within the cup at a location of the lip.

10. The system of claim 7, wherein the cup comprises a lip configured to accept the optical feedthrough, and the optical feedthrough assembly is coupled to the cup at a location of the lip.

11. The system of claim 7, wherein the optical feedthrough assembly comprises a lip configured to mate with an aperture defined by the shell and the optical feedthrough assembly is coupled to the shell at a location of the lip.

12. The system of claim 7, wherein the cup comprises a first cup, the material comprises a first material, the seal disc comprises a first seal disc, and the beam comprises a first beam, the system further comprising:
a second cup that holds a second material; and
a second seal disc that seals the second material within the second cup, wherein the optical feedthrough assembly is coupled to the second cup, and the radiant energy source shines a second beam through the optical feedthrough assembly to puncture the second seal disc to allow the second material to enter the chamber via the discharge port.

13. A method of using the system of claim 1, the method comprising:
sealing a material within a cup using a seal disc, wherein the cup includes a discharge port;
coupling an optical feedthrough assembly to the cup;
coupling the optical feedthrough assembly to a shell that defines a chamber within a medical device; and
applying radiant energy through the optical feedthrough assembly to puncture the seal disc to allow the material to enter the chamber via the discharge port.

14. The method of claim 13, further comprising filling the cup with a measured amount of the material.

15. The method of claim 13, wherein sealing the material with the cup comprises welding the seal disc to the cup at a location between the material and the discharge port.

16. The method of claim 13, wherein coupling the optical feedthrough assembly to the cup comprises welding the optical feedthrough assembly to the cup.

17. The method of claim 13, wherein coupling the optical feedthrough assembly to the shell comprises welding the optical feedthrough assembly to the shell.

18. The method of claim 13, wherein the cup comprises a first cup, the material comprises a first material, and the seal disc comprises a first seal disc, the method further comprising:
sealing a second material within a second cup using a second seal disc;
coupling the optical feedthrough assembly to the second cup; and
applying radiant energy through the optical feedthrough assembly to puncture the second seal disc to allow the second material to enter the chamber via the discharge port.

* * * * *